(12) United States Patent
Rolland et al.

(10) Patent No.: US 8,184,367 B2
(45) Date of Patent: May 22, 2012

(54) DYNAMICALLY FOCUSED OPTICAL INSTRUMENT

(75) Inventors: Jannick Rolland, Chuluota, FL (US); Supraja Murali, Oviedo, FL (US)

(73) Assignee: University of Central Florida Research Foundation, Orlando, FL (US)

( * ) Notice: Subject to any disclaimer, the term of this patent is extended or adjusted under 35 U.S.C. 154(b) by 832 days.

(21) Appl. No.: 11/489,987

(22) Filed: Jul. 20, 2006

(65) Prior Publication Data

US 2011/0051212 A1    Mar. 3, 2011

Related U.S. Application Data

(60) Provisional application No. 60/773,486, filed on Feb. 15, 2006.

(51) Int. Cl.
*G02B 21/00*    (2006.01)

(52) U.S. Cl. ......... 359/383; 359/432; 359/656; 359/665
(58) Field of Classification Search .................... 359/383
See application file for complete search history.

(56) References Cited

U.S. PATENT DOCUMENTS

| | | | |
|---|---|---|---|
| 6,344,930 B1 * | 2/2002 | Kaneko et al. ................. 359/666 |
| 2005/0253055 A1 * | 11/2005 | Sprague et al. ................ 250/234 |
| 2006/0103922 A1 * | 5/2006 | Tsuyuki ......................... 359/383 |

* cited by examiner

*Primary Examiner* — Arnel C Lavarias
(74) *Attorney, Agent, or Firm* — Thomas, Kayden, Horstemeyer & Risley, LLP (57) ABSTRACT

An optical system includes a dynamically focused lens that variably changes focal length to focus light on a material under evaluation at discrete axial depths, and a scanning element that laterally scans the material to focus light on the material at points that are laterally adjacent the axial depth.

16 Claims, 5 Drawing Sheets

DYNAMICALLY FOCUSED OPTICAL INSTRUMENT

CROSS-REFERENCE TO RELATED APPLICATIONS

This application claims priority to copending U.S. provisional application entitled, "Optical Apparatuses and Methods," filed Feb. 15, 2006, having Ser. No. 60/773,486, which is entirely incorporated herein by reference.

BACKGROUND

Cancer is a major public health problem in the United States. According to the American Cancer Society, cancer causes one in four deaths in the United States. The most common form of cancer is skin cancer, which inflicts one in five Americans in their lifetime.

In some cases, skin cancer is curable if detected early and treated properly. Typically, detection is based on surgical biopsy in which a sample of the skin is excised from the patient and is dissected to check for cancerous cells. However, diagnosing skin cancer from an excised sample of skin may be disadvantageous. Because the sample excised is small and the dissection of the sample is random, a diagnosis based on biopsy may be inaccurate. If a cancer diagnosis is made, the patient may be required to return for further biopsies until the extent of the cancer is determined. Complications may also arise as a result of biopsy such as infection, hemorrhage, and the spreading of cancer cells.

An alternative method for diagnosing cancer may exploit non-invasive optical imaging techniques such as optical coherence microscopy (OCM). OCM reconstructs an image of a cross-section of tissue from light that is reflected off of points located on or in the tissue. To ascertain the presence of cancerous cells, the image may be evaluated manually by a physician or electronically by a computer. For accurate diagnosis, it may be desirable for the image to have a relatively high resolution so that individual skin cells can be differentiated. It also may be desirable for the image to extend below the surface of skin, through the entire epidermis in which most skin cancers develop, and into a portion of the dermis into which most skin cancers spread. Because the imaged material is not removed from the patient, it may be desirable to image at a relatively high speed to minimize distortion associated with patient movement, such as breathing. Presently, a need exists for an instrument that can reflect light off of material at such resolution, depth, and speed, and can communicate the light to a system configured to reconstruct an image using OCM.

SUMMARY

In one embodiment, an optical system includes a dynamically focused lens that variably changes focal length to focus light on a material under evaluation at discrete axial depths, and a scanning element that laterally scans the material to focus light on the material at points that are laterally adjacent the axial depth.

In one embodiment, an optical system includes a microscope objective that includes a series of lenses and a dynamically focused lens, the series of lenses narrowing a beam of light entering the microscope objective so that light can be focused by the dynamically focused lens, and the dynamically focused lens variably changing focal length to focus light on a material at an axial depth, the optical system also including a scanning element that laterally scans the material to focus light on the material at points that are laterally adjacent the axial depth, a field lens adjacent the series of lenses that creates an image from light emerging from the series of lenses, scan optics adjacent the scanning element that collimate light traveling toward the scanning element, and a microlenslet array between the field lens and the scan optics that places the image formed by the field lens at the focal plane of the scan optics.

In one embodiment, a method of reflecting light off of points on a two-dimensional cross-section of a material includes focusing on a point of a material under evaluation at a first axial depth, performing a lateral scan at the first axial depth to direct light onto multiple points in a direction lateral to the first axial depth, refocusing on a point of the material under evaluation at a second axial depth, and performing a lateral scan at the second axial depth to direct light onto multiple points in a direction lateral to the second axial depth.

BRIEF DESCRIPTION OF THE FIGURES

The present disclosure may be better understood with reference to the following figures. Matching reference numerals designate corresponding parts throughout the figures, which are not necessarily drawn to scale.

DETAILED DESCRIPTION

Described below are embodiments of a system that can be used to create an image of material using an optical imaging technique. The optical imaging technique processes light that is reflected off of the material by laterally scanning a scanning element and axially refocusing a dynamically focused lens. In some cases, the system images in vivo and in situ skin using optical coherence microscopy (OCM). OCM enables imaging at a relatively high resolution to depths below the surface of the material. By laterally scanning using a high-speed MEMS mirror and axially scanning using a dynamically focused lens, the resolution is maintained for each lateral and axial point imaged, and imaging occurs relatively quickly to reduce image distortion caused by movements such as breathing. In such cases, the system can facilitate diagnosing medical conditions, such as skin cancer, without surgical biopsy.

Figure 1:
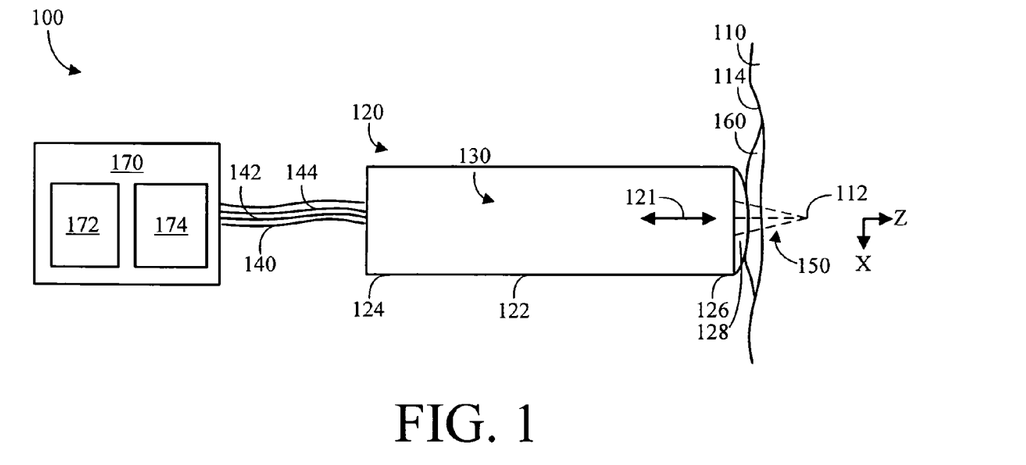
FIG. 1 is a side view of an embodiment of a system that can be used to image a material, the system including an instrument and a control unit.

FIG. 1 is a side view of an embodiment of an imaging system 100 that can be used to image a material 110. The imaging system 100 includes an instrument 120 and a control unit 170. A light source 172 of the control unit 170 communicates light 150 over a cord 140 to the interior of the instrument 120. An optical system 130 within the interior of the instrument 120 focuses the light 150 on a point 112 of the material 110, as described below with reference to FIG. 2 and FIG. 5. The light 150 that is reflected from the point 112 is returned through the optical system 130 and over the cord 140 to the processing system 174 of the control unit 170. The processing system 174 processes the light 150 to create one pixel of an image of the material 110, the pixel of the image corresponding to the point 112 of the material.

In some cases, the material 110 comprises soft tissue. For example, the material 110 can be in vivo and in situ skin tissue, or tissue located on the interior of the body, such as cervical tissue or throat tissue.

As further shown in FIG. 1, the instrument 120 includes a housing 122 that houses the optical system 130. The cord 140 is coupled to a proximal end 124 of the housing 122 and communicates light 150 from the light source 172 to the optical system 130, and from the optical system back to the processing system 174. For example, the cord 140 can comprise a fiber optic cable 142 for transmitting and receiving light 150. The cord 140 may also comprise an electrical wire 144 that communicates electricity to the optical system 130 for the purpose of powering one or more components of the optical system. An imaging window 128 at a distal end 126 of the instrument 120 allows light 150 to pass from the optical system 130 to the material 110 and back to the optical system.

To limit the tendency of a surface 114 of the material 110 to reflect the light 150, an immersion oil or gel 160 having approximately the same refractive index as the material 110 can be placed between the instrument 120 and the material, so that light entering the material passes to the desired depth before being reflected back into the instrument. In embodiments in which the material 110 is skin, a gel 160 having approximately the same refractive index as skin may be used, such as Cargill Labs Optical Gel Code 0607 having a refractive index of about 1.46.

A variety of materials can be used to construct the instrument 120 and the cord 140. For example, the housing 122 of the instrument 120 can be made of a plastic or a metal material. The cord 140 can comprise a flexible lumen that encloses the fiber optic cable 142 and the electrical wire 144. The cord 140 can have an outer diameter that is smaller than the outer diameter of the housing 122, and a length that is long enough to extend from the control unit 170 to the material 110. The imaging window 128 can be a curved plate on the distal end 126 of the instrument 120, although other configurations are possible. For example, the imaging window 128 can be flat. The imaging window 128 can be made of a suitable transparent material, such as glass, sapphire, or a clear, biocompatible polymeric material. In some embodiments, the material used to form the imaging window 128 can also be used to form a portion or the entirety of housing 122.

The instrument 120 can have a variety of shapes. In the embodiment shown in FIG. 1, the instrument 120 is elongated and has a longitudinal central axis which is aligned with the z-axis shown in FIG. 1. In other embodiments, the instrument 120 may be, for example, an optical microscope or a probe suited for in vivo use such as to reflect light off of the cervix or the throat. In such biological applications, biocompatible materials are used to construct the instrument 120 and the cord 140. For example, the housing 122 of the instrument 120 can be made of stainless steel or a biocompatible polymeric material. The cord 140 can be a flexible material such as a biocompatible polymeric material. In some embodiments, the cord 140 can comprise a lumen composed of an inner metallic coil or braid, for example formed of stainless steel or nitinol that is surrounded by an impermeable polymeric sheath. Such an embodiment provides additional column strength and kink resistance to the cord 140 to facilitate advancing the instrument 120 to the location of the material 110. In addition, the housing 122 and/or the cord 140 can be coated with a lubricious coating to facilitate insertion and withdrawal of the instrument 120 to and from the location of the material 110.

The light source 172 can be any light source configured to supply light 150 over the fiber optic cable 142. In some embodiments, the light source 172 may emit high-intensity, low-coherence, near-infrared light. By way of example, the light source 172 comprises a pulsed infrared laser, such as a mode-locked, titanium-doped sapphire (Ti:Sa) femto-laser. The light source 172 can have a central wavelength in the range of approximately 700 nm (nanometers) to 900 nm, for example 800 nm, and a spectral bandwidth of approximately 120 nm. The light source 172 can be tunable to emit high-power pulses that enable two-photon excitation of features contained in the material 110, in which case two-photon fluorescence spectroscopy may be enabled. For example, the light source 172 may emit pulses having a peak power of approximately a few hundred kilowatts (kW).

The processing system 174 may process light 150 reflected from the material 110 using optical imaging techniques such as optical coherence tomography (OCT), OCM, or fluorescence spectroscopy. These imaging techniques allow imaging of materials such as in vivo tissue at high resolution below the material surface. OCM is an optical imaging method that can create high-resolution images of the material, and fluorescence spectroscopy is an optical imaging method that can reveal changes in the biochemistry of the material. OCM images and fluorescence spectroscopy images of materials can be compared or superimposed on top of each other for visual inspection and/or computer analysis. For example, a processing system 174 can be used such as the processing system described in Assignee's currently pending U.S. patent application entitled "Systems and Methods for Performing Simultaneous Tomography and Spectroscopy," filed Apr. 14, 2006, having Ser. No. 11/404,322, which is hereby expressly incorporated by reference in its entirety.

To enable the use of an optical imaging technique such as OCM, the instrument 120 focuses light 150 at an appropriate resolution on discrete points 112 of the material 110 that are at or below the surface 114 of the material. The optical system 130 laterally and axially scans the material 110 with light 150, focusing the light onto laterally and axially adjacent points 112, and reflecting the light back to the processing system 174, which uses the light to reconstruct images of the material pixel-by-pixel. For example, the images may be two-dimensional images of cross-sections of the material 110, such as x-z images (see FIG. 1), which may be aggregated to generate a three-dimensional "image" of the material.

For the purpose of this disclosure, it should be noted that the term "lateral" refers to a direction that is perpendicular to an axis 121 of the instrument 120, such as the x direction indicated in FIG. 1 or a y direction perpendicular to the x and z directions. "Lateral" also refers to a direction that is substantially perpendicular to but is slightly curved with respect to the axis 121 of the instrument 120, as further described below with reference to FIG. 2. Lateral scanning comprises scanning the material 110 in the lateral direction, which may be parallel to its surface 114 or may be substantially parallel but slightly curved with respect to the surface. The term "axial" refers to a direction that is parallel to or is substantially parallel to the axis 121 of the instrument 120, such as the z direction indicated in FIG. 1, and axial scanning comprises scanning in the axial direction, which may be perpendicular or substantially perpendicular to the surface 114 of the material 120.

While lateral and axial scanning are accomplished using components of the optical system 130, these functions can be automated and synchronized by the processing system 174. For example, the processing system 174 may include software that performs these functions, such as Labview Software.

In some embodiments, the optical system 130 of the instrument 120 can achieve micrometer-scale resolution of the material 110 at points 112 that are located on a millimeter-scale depth below the surface 114 of the material. Such resolution may facilitate diagnosis of medical conditions such as the diagnosis of skin cancer. For example, imaging at a micrometer-scale resolution of at least about 5 micrometers (μm) enables resolving individual cells of the epidermis, such as basal cells, which may facilitate differentiation of normal skin cells from cancerous skin cells. Further, imaging to millimeter-scale depths may be desirable. For example, the material may be imaged to an axial depth in the range of about 0.5 mm to about 2 mm. For example, imaging to a depth of at least about 1 mm enables imaging through the entire epidermis, which is the layer of the skin in which most types of skin cancer develop, and may enable an evaluation of the vertical depth of the cancer, which could be indicative of the extent and significance of the cancer.

Figure 2:
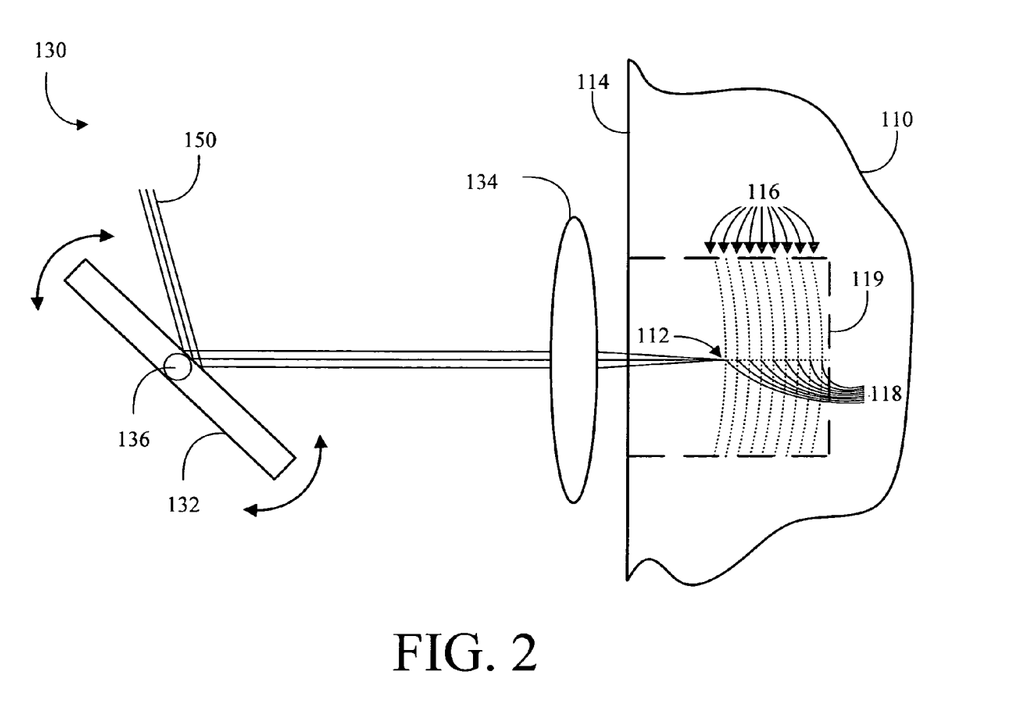
FIG. 2 is a side view of a first embodiment of an optical system that can be used in the instrument shown in FIG. 1.

FIG. 2 is a side view of a first embodiment of an optical system 130 that can be used in the instrument 120 shown in FIG. 1. The optical system 130 includes a scanning element 132 and a dynamically focused lens 134. Together the scanning element 132 and the dynamically focused lens 134 laterally and axially scan light 150 relative to the material 110, focusing the light on points 112 of a cross-section of the material 119 at or below the surface 114 of the material, and reflecting the light back to the processing system 174. The optical system 130 also invariably maintains resolution as the material 110 is laterally and axially scanned.

Lateral scanning is accomplished by scanning the scanning element 132, which redirects the light 150 to laterally adjacent points 112 of the material 110 along a chosen lateral scan 116. The light 150 reflected from points 112 of the material 110 along the lateral scan 116 may be used by the processing system 174 to construct a one-dimensional image of the material along the lateral scan 116. Axial scanning is accomplished by readjusting the dynamically focused lens 134 to alter the focal length of the lens, such that the lens is properly focused for the chosen axial depth 118. At that axial depth 118, a lateral scan 116 is performed by scanning the scanning element 132. Once the lateral scan 116 is complete, the dynamically focused lens 134 may be refocused for a new axial depth 118, and a further lateral scan 116 is performed at that axial depth 118 by scanning the scanning element 132. In this manner, light 150 collected for lateral scans 116 at various axial depths 118 is combined and processed to produce a two-dimensional image of the material 110 along a two-dimensional cross-section 119 that extends below the surface 114 of the material.

The scanning element 132 can comprise a scanning minor such as a micro-electro-mechanical-system (MEMS) minor. In cases in which the scanning element 132 is a MEMS mirror, the MEMS minor may have a single axis 136 and may rotate about that axis in the manner depicted in FIG. 2. In other embodiments, the scanning element 132 can rotate about two axes (not shown) or the optical system 130 may have two single-axis MEMS to enable scanning in multiple directions (not shown).

The resolution of the instrument 120 does not vary as the scanning element 132 rotates about the axis 136 to direct the light 150 onto discrete points 112 of a lateral scan 116. As shown in FIG. 2, each point 112 on the lateral scan 116 may be a fixed distance from the axis 136 of rotation of the scanning element 132, such that the lateral scan 116 has a slight radius of curvature. As a result, the resolution of the instrument 120 is invariably maintained for each point 112 on a chosen lateral scan 116. It should be noted that the radius of curvature is exaggerated in FIG. 2 for illustrative purposes, and that the lateral scan 116 may be substantially linear in cases in which the cross-section 119 has a lateral dimension that is relatively small in comparison with the fixed distance from the axis 136 of rotation.

The distance between points 112 on the lateral scan 116 may vary according to the desired resolution of the instrument 120. For example, the distance between points 112 may be about one-half the desired resolution. In cases in which the desired resolution is about 5 μm, the distance between points on the lateral scan may be about 2.5 μm.

To accomplish the axial scanning, the dynamically focused lens 134 variably changes focal length to alter the depth of focus of the lens. Because the dynamically focused lens 134 is refocused for each axial depth 118, the lens maintains an invariant resolution throughout the axial scanning. In some embodiments, a dynamically focused lens 134 that refocuses relatively quickly is preferred. For biological applications, refocusing of the dynamically focused lens 134 may occur in about 100 nanoseconds (ns) to 1 ms (milliseconds). Such rapid refocusing can be achieved, for example, by a lens that refocuses without mechanical translation, i.e., physical movement in the axial direction. Such a lens remains axially stationary, unlike a conventional lens that refocuses by axially translating bulk optics that may be relatively time consuming to move. Therefore, a dynamically focused lens that refocuses without axial translation enables relatively fast refocusing. Examples of lenses that do not mechanically translate include liquid lenses and liquid crystal lenses, both of which are configured to refocus on a new axial depth without the mechanical translation of bulk optics.

The imaging speed of the instrument 120 may be about 1 frame per second to more than about 30 frames per second, each frame corresponding to a single cross-section 119 of the material 110. The imaging speed may be a function of the lateral and axial dimensions of the cross-section 119 as well as the desired resolution of the resultant image. The imaging speed may also be a function of the number of axial depths 118 at which lateral scans 116 are to be performed, as well as the time consumed per axial depth 118 by refocusing the dynamically focused lens 134 and performing the lateral scan 116. In other words, there is a relationship among the imaging speed, the size of the cross-section 119, the desired resolution, the number of axial depths 118, and the speed of refocusing and laterally scanning per axial depth 118.

Figure 3:
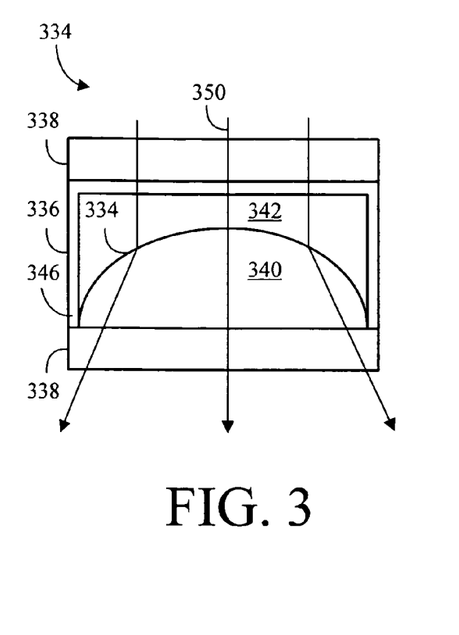
FIG. 3 is a side view of an embodiment of a liquid lens that can be used in the optical system.
Figure 4:
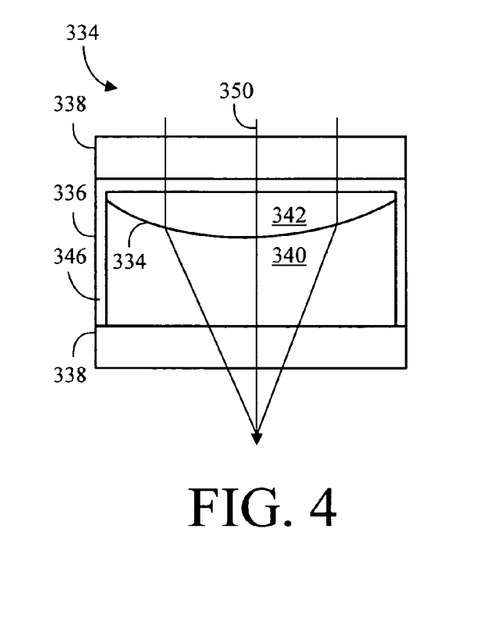
FIG. 4 is a side view of the liquid lens shown in FIG. 3, illustrating the lens at a different focus.

FIG. 3 is a side view of an embodiment of a liquid lens 334 that can be used in the optical system 130 shown in FIG. 2. The liquid lens 334 comprises a tubular casing 336 with transparent end caps 338. Light 350 may pass through a first end cap 338 into the lens 334 and then out of the lens through a second end cap 338. Within the tubular casing 336 are a first liquid 340 and a second liquid 342. The liquids 340 and 342 are immiscible liquids having approximately the same density but different refractive indexes. The first liquid 340 may be electrically conductive and the second liquid 342 may be nonconductive. For example, the first liquid 340 may be an electrically conductive aqueous solution and the second liquid 342 may be a nonconductive oil. Because the liquids 340 and 342 are immiscible with respect to each other, a meniscus 344 forms between the two liquids, and a radius of curvature of the meniscus determines the focal length of the lens. The liquid lens 334 may be refocused by altering the radius of curvature of the meniscus 344, which may be accomplished by applying a voltage to a hydrophobic coating 346 that covers the interior of the tubular casing 336 and one of the end caps 338. Applying a voltage may alter the hydrophobicity of the coating 346 causing the electrically conductive first liquid 340 to become more or less resistant to the hydrophobic coating 346. As the first liquid 340 moves into greater or lesser contact with the hydrophobic coating 346, the radius of curvature of the meniscus 344 changes and the focal length of the lens 334 is adjusted, as shown in FIG. 4. Therefore, such a liquid lens 334 can be refocused electrically, unlike a standard lens that refocuses by mechanical translation. In another embodiment of the optical system 130, the dynamically focused lens 134 is a liquid crystal lens. Such lenses are made by companies such as Philips and Varioptic of Lyon, France.

As stated above, the optical system 130 may laterally and axially scan light 150 that is focused at a high resolution on points 112 that lie below the surface 114 of the material 110. In such an embodiment, high resolution is enabled by the dynamically focused lens 134, which may have an f-number that is between 1 and 100. High resolution is also enabled by using an optical system 130 having a relatively high numerical aperture. For example, the numerical aperture of the optical system 130 may be in the range of about 0.2 to about 0.9. In one embodiment, the numerical aperture may be about 0.28, although other numerical apertures that enable high-resolution imaging could be used.

High resolution may also be enabled by the wavelength of the light 150 that is focused on the material 110, such as NIR light. NIR light also enables imaging at depths below the surface 114 of the material 110, especially in the case of skin, because NIR light falls within the "diagnostic window" of skin in which absorption by skin is relatively low. In the case of skin, the resolution of the instrument 120 may be at least about 5 μm, as mentioned above.

Figure 5:
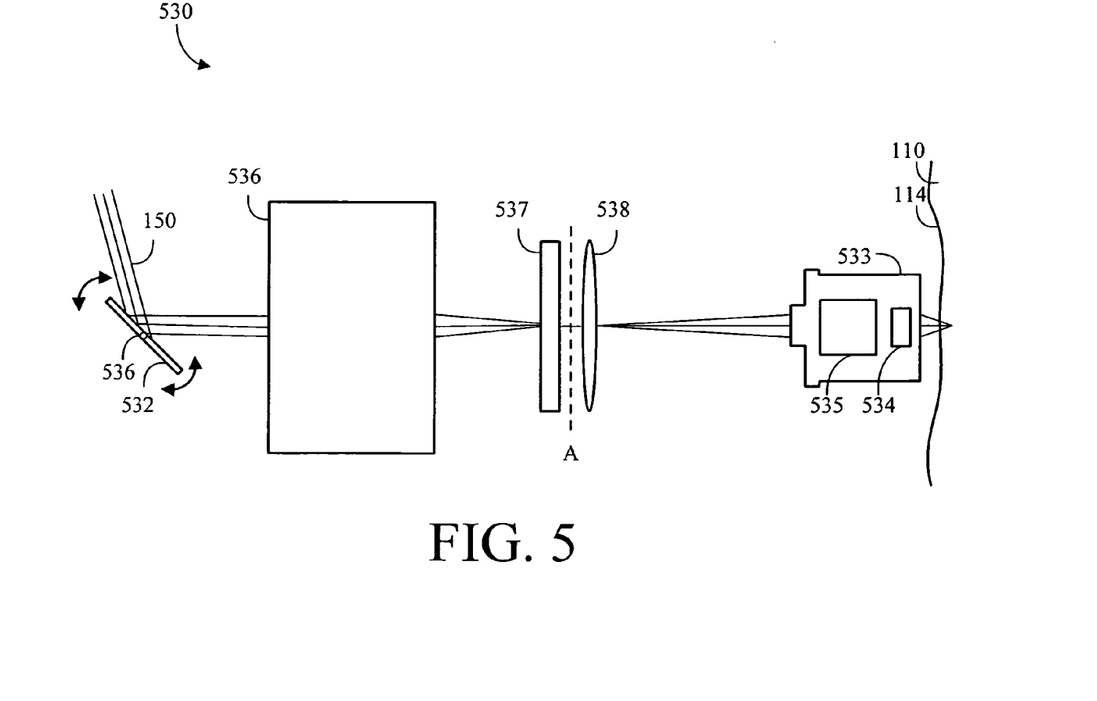
FIG. 5 is a side view of a second embodiment of an optical system that can be used in the instrument shown in FIG. 1.

FIG. 5 is a side view of a second embodiment of an optical system 530 that can be used in the instrument 120 shown in FIG. 1. Like the optical system 130, the optical system 530 can facilitate high-resolution imaging below the surface 114 of the material 110. In addition, the optical system 530 is configured to scan relatively quickly and to be relatively compact. For example, the optical system 530 may scan at a rate in the range of about 1 frame per second to about 30 frames per seconds. Because of the reduced size, the optical system 530 may be small enough to fit inside a handheld instrument 120. In cases in which the material 110 is in vivo tissue, a compact, handheld instrument may be conducive to imaging in a clinical environment. By quickly imaging the tissue, such an instrument reduces errors associated with movements by the patient, such as breathing or heart beating.

The optical system 530 includes a scanning element 532, a microscope objective 533, and optics between the scanning element 532 and the microscope objective 533 that reduce the size and increase the speed of the optical system. These optics include scan optics 536, a microlenslet array 537, and a field lens 538.

The microscope objective 233 includes a series of lenses 535 and the dynamically focused lens 534, which magnify the material 110. The light 150 that enters the microscope objective 533 is bent by the series of lenses 535 so that the beam is properly sized to enter the dynamically focused lens 534 and so that the dynamically focused lens can focus the light at a high resolution. As mentioned above, the dynamically focused lens 534 changes its effective focal length relatively quickly. For example, the dynamically focused lens 534 may refocus without the relatively slow axial translation of bulk optics, as described above with reference to FIG. 2. To further improve speed, the dynamically focused lens 534 is placed close to the material 110, where the light 150 is a small beam. This allows a relatively small dynamically focused lens 534 to be used, reducing the size of the overall system 530 and increasing the speed at which the lens may be refocused. For example, in cases in which 500 lateral scans are performed at 500 discrete axial depths, the dynamically focused lens 534 may refocus in at least about 66 μs to enable imaging at a video rate of at least about 30 frames per second.

In the embodiment shown in FIG. 5, the dynamically focused lens 534 comprises a liquid lens, which may refocus at a relatively faster speed than a liquid crystal lens. For example, the liquid lens may require less than about 66 μs to refocus. Further, the liquid lens may be relatively small, having a diameter of about 3 mm. The microscope objective 533 is placed about 25 mm from the material 110 and has a magnification of about 10×.

Figure 6:
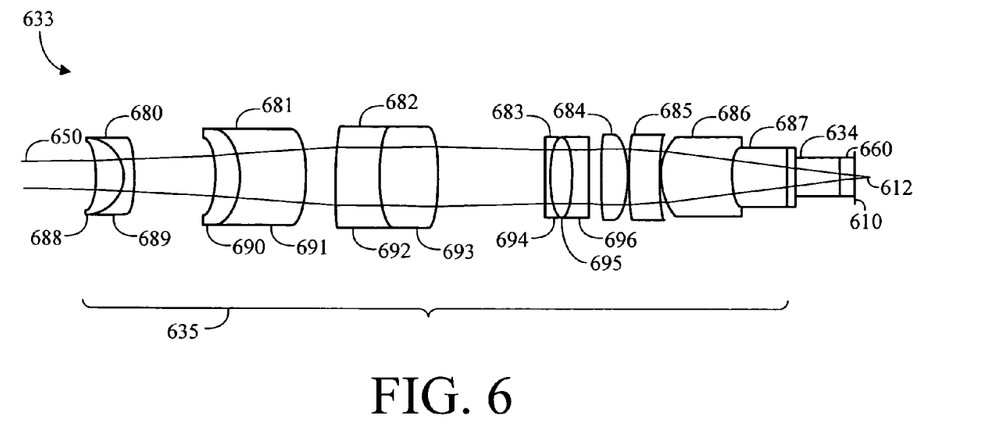
FIG. 6 is a side view of an embodiment of a microscope objective that can be used in the optical system shown in FIG. 5.

FIG. 6 is a side view of an example embodiment of a microscope objective 633 that can be used for the microscope objective 533 shown in FIG. 5. Although FIG. 6 illustrates a particular arrangement, alternative configurations can, of course, be used. Upon entering the microscope objective 633, the light 650 passes through the series of lenses 635 that condition the light to be focused by the dynamically focused lens 634 at a high numerical aperture. The series of lenses 635 includes imaging lens systems that smoothly bend the light such that a high-quality image can be formed. The imaging lens system 680 includes a doublet lens 688 and lens 689. The imaging lens system 681 includes a doublet lens 690 and a lens 691. The imaging lens 682 includes a doublet lens 692 and a lens 693. The imaging lens system 683 includes a triplet lens 694, a lens 695, and a lens 696. Doublets and triplet lenses are used to control chromatic aberrations. Collectively, the series of lenses 635 condition the light 150 by bending the light rays such that the beam is properly sized to enter the dynamically focused lens 634. For example, as shown in FIG. 6, a wide beam of light 650 may be narrowed such that the light enters the dynamically focused lens 134, which focuses the light 650 onto a point 612 of the material 610. In some embodiments, the light 650 also passes through the gel 660 before being reflected off of the point 612.

With reference back to FIG. 5, the field lens 538 is positioned adjacent the microscope objective 533. By positioning the field lens 538 relatively close to the image point of the microscope objective 533, magnification by the field lens is reduced. The field lens 538 creates a image located at the focal plane A, and modifies off-axis light emerging from the microscope objective 533 into a telecentric beam, collimating the chief ray and reducing off-axis aberrations. The field lens 538 also slightly reduces the size of the beam of light 550 so that a smaller diameter microlenslet array 537 can be used, further reducing the size of the optical system 530. In the embodiment shown, the field lens 538 is about 100 mm from the microscope objective 533, having a diameter of about 20 mm, an f-number of about 2.5, and a magnification of about 1×.

The microlenslet array 537 comprises an array of microlenses that is positioned between the field lens 538 and the scan optics 536. The virtual image formed by the field lens 538 at the focal plane A is placed by the microlenslet array 537 at the focal plane of the scan optics 536. The focal plane A falls within the focal length of each lenslet, which is a relatively short focal length due to the small size of each lenslet. Therefore, the microlenslet array 537 shortens the length of the optical system 530. In the embodiment shown in FIG. 5, the microlenslet array 537 is positioned about 1 mm to about 10 mm from the field lens 538. Each lenslet has a diameter of about 20 µm, an f-number of about 5 and a focal length that is on a micrometer scale.

The scan optics 536 are telecentric scan optics and are positioned adjacent to the microlenslet array 537. The scan optics 536 collimate light 150 from the microlenslet array 537 so that a collimated beam is returned by the scanning element 532 into the fiber optic cable 142 (not shown). In some embodiments, the scan optics 536 are positioned about 40 mm from the microlenslet array 537, having a diameter of about 20 mm and a f-number of about 2.

As explained above with reference to FIGS. 1 and 2, the scanning element 532 can be, for example, a mirror such as a MEMS mirror that laterally scans the material 110 using light 150 provided over the fiber optic cable 142 (not shown). The scanning element 532 may be powered by electricity supplied over the cord, and may be controlled by software within the processing system 174 (not shown). For quick scanning, the scanning element 532 is sized and configured to move relatively quickly. For example, in embodiments in which the scanning element 532 is a MEMS mirror, the MEMS mirror may be relatively small to enable relatively fast scanning because a relatively small mirror has less volume and mass and is therefore easier to move.

In embodiments in which imaging across three dimensions is not desired, a single-axis MEMS mirror may be used instead of a dual-axis MEMS mirror because a single-axis MEMS mirror rotates at a relatively faster rate than a dual-axis MEMS mirror. For example, in FIG. 5 the scanning element 532 is a single-axis MEMS mirror having dimensions of about 1 mm by about 1 mm. The scanning element may be configured to scan at a rate of at least about 10 kHz. In some cases, the MEMS mirror 532 can rotate through a range of angles sufficient to laterally scan approximately 1 mm. For example, the MEMS mirror 532 can rotate through about a 10 degree range of angles. In some embodiments, the MEMS mirror 532 is positioned about 40 mm from the scan optics 536.

Additionally, the numerical aperture of the optical system 530 may be in the range of about 0.2 to about 0.9. In the illustrated embodiment, the numerical aperture is about 0.3 to enable high-resolution focusing.

Such an optical system 530 may image at video rates, such as at rates of at least about 30 frames per second. For cross-sections of the material having a lateral dimension and an axial dimension in the range of about, for example, 0.5 mm to about 2 mm, the optical system 530 may be able to image at a micrometer scale resolution, such as a resolution of at least about 5 µm. Such parameters may enable imaging a material such as, for example, in vivo skin.

Figure 7:
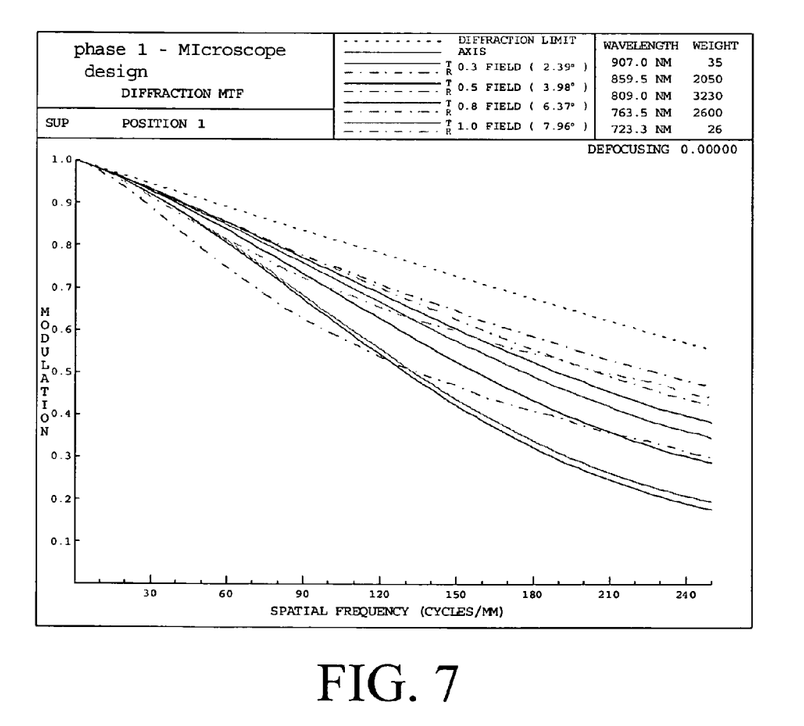
FIG. 7 is a modulation transfer function of the optical system shown in FIG. 5, corresponding to the optical system focused on the surface of the material.
Figure 8:
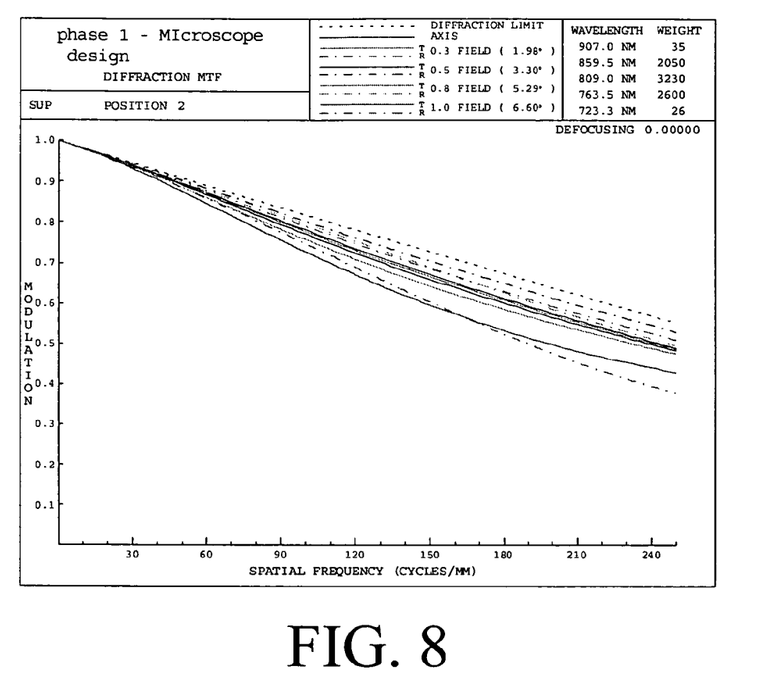
FIG. 8 is a modulation transfer function of the optical system shown in FIG. 5, corresponding to the optical system focused one millimeter below the surface of the material.
Figure 9:
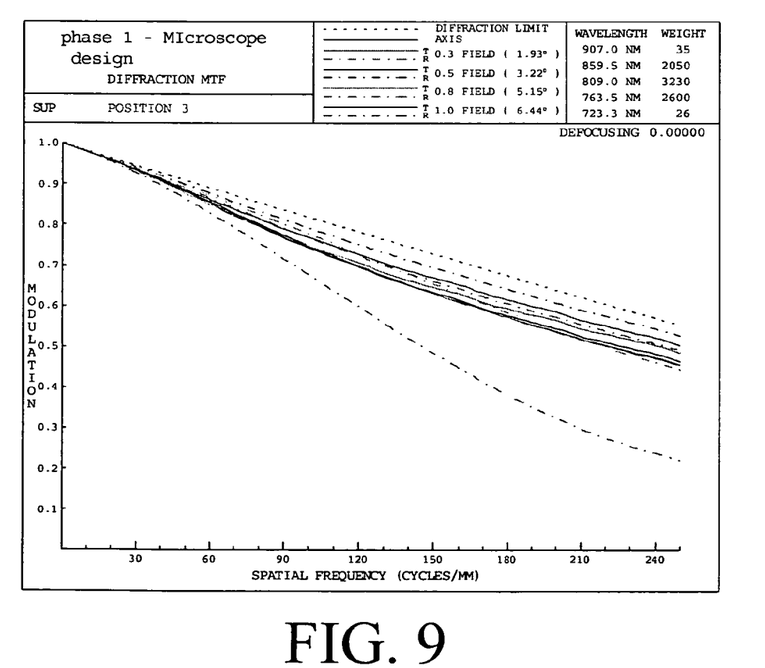
FIG. 9 is a modulation transfer function of the optical system shown in FIG. 5, corresponding to the optical system focused two millimeters below the surface of the material.

FIGS. 7-9 show modulation transfer functions (MTF) for the optical system 530 shown in FIG. 5 focused at various axial depths. FIG. 7 is the MTF for the optical system 530 focused on the surface of the material, at an axial depth of 0 mm, FIG. 8 is the MTF for the optical system focused at an axial depth of 1 mm below the surface of the material, and FIG. 9 is the MTF of the optical system focused at an axial depth of 2 mm below the surface of the material. Plotted in each graph is the diffraction limit (dashed line) and frequency response curves of tangential (T) and sagittal (R) light rays. In each graph, the MTF curves closely follow the diffraction limit curve, which is an indication that the optical system 530 is well designed.

Figure 10:
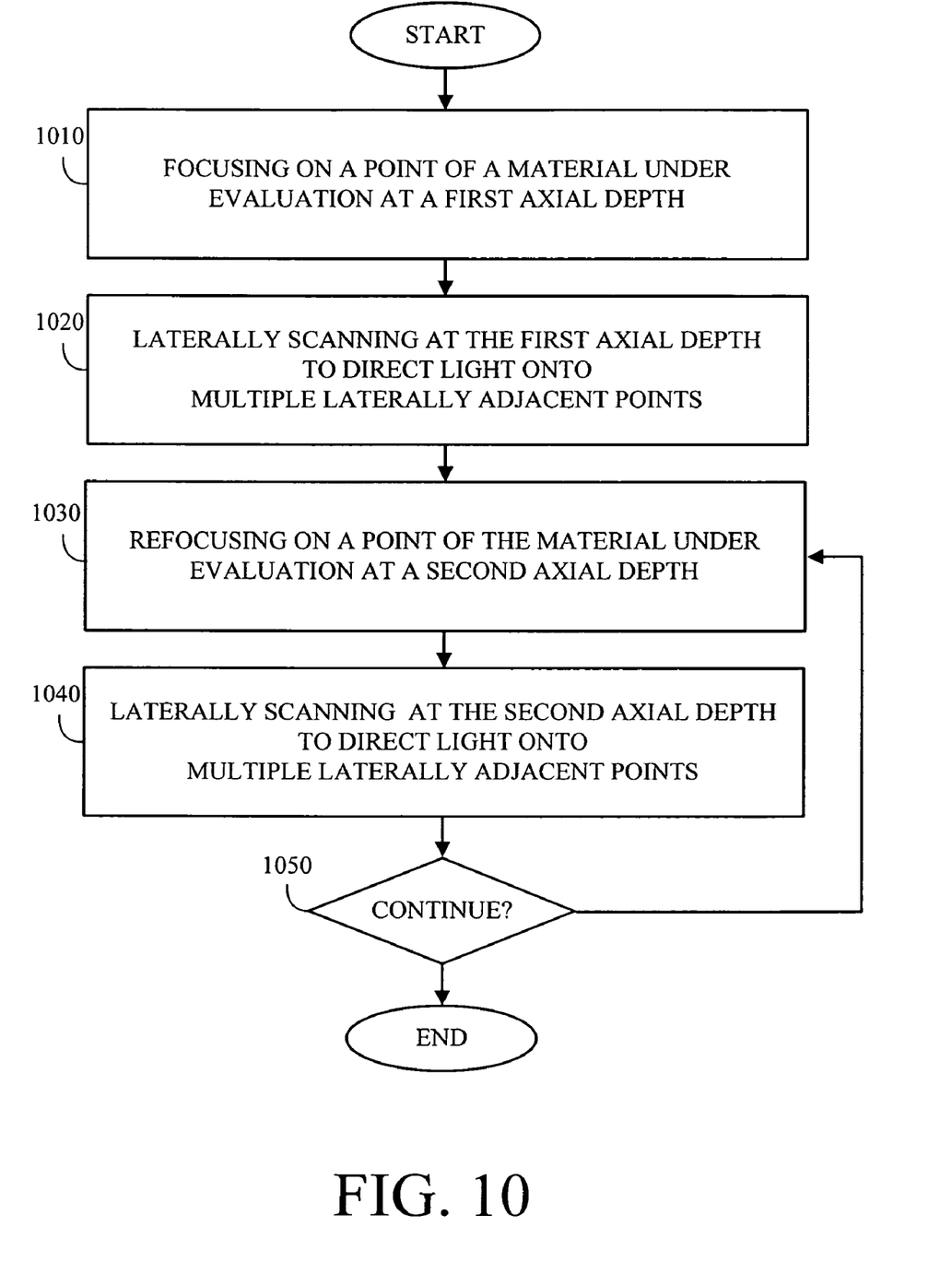
FIG. 10 is an embodiment of a method of reflecting light off of points on a two-dimensional cross-section of a material.

FIG. 10 is an embodiment of a method 1000 of reflecting light off of points of a material. In block 1010, a first point of a material under evaluation is focused on using light, the first point being at a first axial depth below the surface of the material and the light being, for example, NIR light. Focusing on the point can comprise focusing a dynamically focused lens to change the focal length of the lens. The dynamically focused lens can be, for example, a liquid lens or a liquid crystal lens. Focusing on the point may occur relatively quickly, such as in cases in which the lens focuses without the axial translation of bulk optics. In some embodiments, focusing on the point may comprise focusing at a high resolution, such as by focusing NIR light using a lens having a high numerical aperture.

In block 1020, a lateral scan is performed at the first axial depth to direct light onto points in a direction lateral to the first axial depth. Performing the lateral scan can comprise scanning a scanning element. For example, the scanning element can be a minor such as a MEMS mirror and scanning the scanning element can comprise rotating the MEMS minor such that the light is redirected onto laterally adjacent points. In some embodiments, directing light onto the points can comprise reflecting light off of the points. The light reflected off of the points can be returned to a processing system that processes the light using an optical imaging technique. In block 1030, a second point of the material is focused on, the second point being at a second axial depth below the surface of the material. Focusing on the second point can comprise focusing as described above with reference to block 1030, such as by changing the focal length of a dynamically focused lens to be focused at the second axial depth. In block 1040, a lateral scan is performed at the second axial depth to direct light onto points in a direction lateral to the second axial depth. Laterally scanning at the second depth can comprise scanning as described above with reference to block 1030. For example, the MEMS minor can be rotated about the axis. Light may be reflected off of the points and may be returned to a processing system. In block 1050, it is determined whether to continue. Block 1040 is returned to if the method 1000 is continued. Otherwise, the method 1000 ends.

An embodiment of the instrument described above can facilitate rapid and accurate diagnosis of cancer by enabling imaging of tissue at a high and invariant axial and lateral resolution at and below the tissue surface. By scanning quickly, the instrument reduces errors that are associated with patient movement. Specifically, for example, embodiments of the instrument can scan a material measuring about 1 mm laterally by about 1 mm axially using NIR light having a wavelength of about 800 nm, at a resolution of about 5 µm. In such case, light can be reflected off about 400 points per lateral scan, each point being about 2.5 µm from the next laterally adjacent point. In embodiments in the lateral scan is performed using a 15 Khz MEMS mirror, refocusing the dynamically focusing lens and performing the lateral scan consumes about 66 µs. Therefore, the entire scan requires 26 ms, and a resolution of 5 µm is invariably maintained both axially and laterally. While particular embodiments of optical system have been disclosed in detail in the foregoing description and drawings for purposes of example, those skilled in the art will understand that variations and modifications may be made without departing from the scope of the disclosure. All such variations and modifications are intended to be included within the scope of the present disclosure.

The invention claimed is:

1. An optical system comprising:
   a microscope objective that includes a series of lenses and a dynamically focused lens, the series of lenses configured to narrow a beam of light entering the microscope objective so that light can be focused by the dynamically focused lens, and the dynamically focused lens configured to variably change focal length without axial translation to focus light on a material at an axial depth;
   a scanning element configured to laterally scan the material to focus light on the material at points that are laterally adjacent the axial depth;
   a field lens adjacent the series of lenses configured to create an image from light emerging from the series of lenses;
   scan optics adjacent the scanning element configured to collimate light traveling toward the scanning element;
   a microlenslet array between the field lens and the scan optics configured to place the image formed by the field lens at the focal plane of the scan optics; and
   a processing system configured to automatically control both the dynamically focused lens and the scanning element to sequentially perform lateral scans of the material at multiple axial depths.

2. The optical system of claim 1, wherein the optical system maintains a resolution of at least about 5 micrometers for each axial depth and lateral scan.

3. The optical system of claim 2, wherein the optical system laterally and axially scans the two-dimensional cross-section at a video rate in the range of about 30 frames per second.

4. The optical system of claim 1, wherein the scanning element is a single-axis MEMS mirror that is configured to scan by rotating about an axis.

5. The optical system of claim 4, wherein the MEMS mirror rotates at a rate at least about 10 kHz.

6. The optical system of claim 1, wherein the dynamically focused lens refocuses in about 100 nanoseconds to about 66 milliseconds.

7. The optical system of claim 1, wherein the dynamically focused lens is one of a liquid lens or a liquid crystal lens.

8. The optical system of claim 7, wherein the optical system has a numerical aperture in the range of about 0.2 to about 0.9.

9. The optical system of claim 1, wherein the system is configured to focus light at a resolution of at least about 5 micrometers.

10. The optical system of claim 1, wherein the light is near infrared light having a wavelength in the range of about 700 nm to about 900 nm.

11. The optical system of claim 1, wherein:
    the series of lenses is configured to condition light from the field lens such that the light can be focused by the optical system at a high numerical aperture; and
    the field lens modifies off-axis light emerging from the microscope objective into a telecentric beam, collimates the chief ray and reduces off-axis aberrations, and narrows the beam of light.

12. The optical system of claim 1, wherein the microlenslet array includes an array of microlenses, each of the microlenses having a micrometer-scale focal length.

13. The optical system of claim 12, wherein:
    the optical system has a numerical aperture of about 0.3;
    the microscope objective has a magnification of about 10X;
    the field lens has an f-number of about 2.5 and a magnification of about 1X;
    each microlens has a diameter of about 20 µm and an f-number of about 5;
    the scan optics have a diameter of about 20 mm and a f-number of about 2; and
    the scanning element is about 40 mm from the scan optics, the scan optics are about 40 mm from the microlenslet array, the field lens is about 100 mm from the microscope objective, and the microscope objective is about 2.5 mm from the sample.

14. The optical system of claim 1, wherein the processing system uses an optical imaging technique to create an image of the material from light reflected off of points on the material, each pixel of the image corresponding to a point on the material.

15. The optical system of claim 1, wherein the system is configured to reflect light off of points of a material at a resolution of about 5 micrometers.

16. The optical system of claim 1, wherein the optical system laterally and axially scans a two-dimensional cross-section of a material at a video rate in the range of about 30 frames per second.

* * * * *